(12) United States Patent
Nielsen

(10) Patent No.: US 7,731,856 B2
(45) Date of Patent: Jun. 8, 2010

(54) METHOD AND SYSTEM FOR TREATING WASTE MATTER FROM ANIMALS, UREA-RICH AND UREA-LEAN WASTE-MATTER PRODUCTS, AND USES THEREOF

(75) Inventor: Dennis Wowern Nielsen, Rønne (DK)

(73) Assignee: Waste 2 Green, LLC, Cocoa, FL (US)

( * ) Notice: Subject to any disclaimer, the term of this patent is extended or adjusted under 35 U.S.C. 154(b) by 140 days.

(21) Appl. No.: 10/565,992

(22) PCT Filed: Jul. 26, 2004

(86) PCT No.: PCT/DK2004/000513

§ 371 (c)(1),
(2), (4) Date: Jul. 17, 2006

(87) PCT Pub. No.: WO2005/009925

PCT Pub. Date: Feb. 3, 2005

(65) Prior Publication Data

US 2006/0243671 A1 Nov. 2, 2006

(30) Foreign Application Priority Data

Jul. 25, 2003 (DK) ............................... 2003 01104

(51) Int. Cl.
*C02F 1/68* (2006.01)
*C05F 3/00* (2006.01)
*C05C 9/00* (2006.01)
*C07C 273/00* (2006.01)

(52) U.S. Cl. .................. 210/749; 210/767; 210/916; 71/15; 71/28; 119/161; 564/3; 564/73

(58) Field of Classification Search .................. 210/632, 210/749, 741, 808, 903, 916, 767; 71/15, 71/21, 12, 14, 28; 435/183, 184, 188; 119/161, 119/174; 564/3, 63, 73
See application file for complete search history.

(56) References Cited

U.S. PATENT DOCUMENTS 154,092 A * 8/1874 Scott .............................. 71/13

(Continued)

FOREIGN PATENT DOCUMENTS

CH          202557          4/1939

(Continued)

OTHER PUBLICATIONS

International Search Report PCT/DK2004/000513 dated 11 Oct. 2004.
D.W. Nielsen and G. Jonsson: Separation Science and Technology, 29(9) pp. 1165-1182.
L.L. Williams: Amino Resins and Plastics. In Krik-Othmer: Encyclopedia of Chemical Technology, vol. 2, pp. 604-637.

(Continued)

*Primary Examiner*—Matthew O Savage
*Assistant Examiner*—Lucas Stelling
(74) *Attorney, Agent, or Firm*—Ostrolenk Faber LLP

(57) ABSTRACT

A method of treating waste matter from animals, the method comprising: a) collecting waste matter from the animals; b) inhibiting urease activity in said collected waste matter; and c) separating said urease-activity inhibited waste matter into a urea-rich fraction and a urea-lean fraction; a system for treating waste matter from animals; a urea-lean biogas fuel product; a urea-rich animal waste-matter product; a method of controlling the content of nitrogen in manure from animals; a method of reducing gaseous ammonia in stables for animals; a stable for animals; a biogas reactor system for producing biogas from waste matter from animals; a method of producing urea from waste matter of animals; a method of producing urea formaldehyde; and a method of producing biogas fuel from waste matter of animals.

14 Claims, 3 Drawing Sheets

U.S. PATENT DOCUMENTS

| | | | |
|---|---|---|---|
| 3,073,693 A | 1/1963 | Nielsson | 71/13 |
| 3,227,543 A | 1/1966 | O'Donnell | 71/28 |
| 3,388,989 A | 6/1968 | Sor | |
| 3,565,599 A | 2/1971 | Sor et al. | |
| 3,644,642 A * | 2/1972 | Wilson et al. | 514/574 |
| 3,677,736 A * | 7/1972 | Formaini | 71/28 |
| 3,743,496 A | 7/1973 | Seltzer | 71/21 |
| 3,826,638 A | 7/1974 | Whitman | 71/21 |
| 3,976,465 A | 8/1976 | O'Donnell | 71/13 |
| 4,349,572 A * | 9/1982 | Larson et al. | 426/335 |
| 6,287,550 B1 * | 9/2001 | Trinh et al. | 119/173 |
| 6,916,426 B2 * | 7/2005 | Van Slyke et al. | 210/903 |
| 2001/0047963 A1 * | 12/2001 | Morita et al. | 210/651 |
| 2002/0158024 A1 | 10/2002 | Van Slyke et al. | 210/696 |

FOREIGN PATENT DOCUMENTS

| | | |
|---|---|---|
| DE | 227 949 | 10/1985 |
| DE | 101 54 165 | 5/2003 |
| DK | 116452 | 1/1970 |
| GB | 1 483 150 | 8/1977 |
| GB | 1 567 773 | 5/1980 |

OTHER PUBLICATIONS

Internet printout regarding Urease: http://www.worthingthon-biochem.com/URC7default.html.

Enzyme Handbook 4, Class 3: Hydrolases, Springer-Verlag, Berlin. Entry 3.5.1.5, Urease.

Ullmann's Encyclopedia of Industrial Chemistry, vol. A27, VVH Verlagsgesellschaft (1996) pp. 333-365.

Database Abstract XP-002295885 (SK 14596).

H. Diem and G. Matthias: Amino Resins. In Ullmann's Encyclopedia of Industrial Chemistry vol. A2 pp. 115-141.

* cited by examiner

METHOD AND SYSTEM FOR TREATING WASTE MATTER FROM ANIMALS, UREA-RICH AND UREA-LEAN WASTE-MATTER PRODUCTS, AND USES THEREOF

CROSS REFERENCE TO RELATED APPLICATION

The present application is a 35 U.S.C. §§371 national phase conversion of PCT/DK2004/000513, filed Jul. 26, 2004, which claims priority of Danish Application No. PA2003 01104, filed Jul. 25, 2003. The PCT International Application was published in the English language.

BACKGROUND OF THE INVENTION

1. Technical Field

The present invention relates to a method and system for treating waste matter from animals, in particular farm animals; a urea-lean biogas fuel product; a urea-rich animal waste-matter product; and uses thereof, in particular in a method of controlling the content of nitrogen in manure, in a method of reducing gaseous ammonia in stables, in a stable for farm animals, in a biogas reactor system for producing biogas, in a method of producing urea from waste matter, in a method of producing urea formaldehyde, and in a method of producing biogas fuel from waste matter.

2. Background Art

Commercial utilisation of livestock in the production of meat from e.g. pig, cattle, or sheep produces large quantities of animal waste matter to be disposed.

Present methods of disposing animal waste matter include recycling thereof through the agricultural system e.g. by storage and spreading the animal waste matter such as animal manure on land, optionally spreading it on land after treatment thereof for removing excess polluting nutrients which cannot be absorbed in the soil. However, although such treatment methods provide improved disposable waste matter having reduced amounts of nutrients such as phosphorous, nitrogen-containing compounds, and accumulating minerals such as copper, the treated waste matter is still spread on the land. Consequently, lack of land sites with suitable capacity and risks of excess fertilisation or excess manuring resulting in undesired pollution put an upper limit to the amount of treated animal waste matter that can be disposed this way. Additionally, removed nutrients and minerals in the waste matter treatment would have to be disposed.

Consequently, there is a need for a method and apparatus for disposing animal waste matter which does not depend, or does not totally depend on disposal through the agricultural system.

PRIOR ART DISCLOSURES

U.S. Pat. No. 3,388,989 discloses a fertilizer composition comprising urea, urease inhibitor and hydrocarbon binder; said urease inhibitor being a soluble heavy metal having an atomic weight larger than 50, preferably selected from the group consisting of copper, molybdenum, cobalt, zinc, manganese, silver, lead and mercury in form of water-soluble or partially water-soluble sulphates, chlorides, chlorates, nitrates, and acetates; a soluble boron salt, preferably sodium or potassium borate; or a fluorine metal salt, preferably sodium and potassium fluoride; or formaldehyde. Specifically disclosed examples of urease inhibitors are cupper sulphate, lead acetate, and formaldehyde. It should be noted that according to this prior art formaldehyde reacts with the hydrolysis product ammonia whereby the result of the urease activity is reduced but the urease catalytic activity is not inhibited as such. This prior definition of formaldehyde does not fall within the meaning of a urease inhibitor according to the present invention.

U.S. Pat. No. 3,565,599 discloses a nitrogen-containing fertilizer having reduced evaporation of ammonia, the fertilizer comprising urea, urease inhibitor and a hydrophobic substance; said urease inhibitor preferably comprises a boron-containing compound such as borates, boric acid; other urease inhibitors include heavy metals such as ions of copper, cobalt, silver, mercury, manganese, zinc, cadmium, nickel and lead; fluorides, halogens and cyanides such as sodium fluoride, sodium iodide, sodium bromide and sodium cyanide; sulphuric acid and quinones, aldehydes such as formaldehyde, urea derivatives such as methyl-, ethyl- and thio-forms of urea, alkyl and carbamates such as dialkyl dithiocarbamates, organic and inorganic acids, biocides such as phenol compounds, pyridine compounds and others.

U.S. Pat. No. 3,743,496 discloses a method of treating veterinary animal and fowl faeces, optionally in presence of litter and the animals, for elimination of ammonia and other odours and suppression of bacterial content, the method comprising combining faeces and formaldehyde, said combination giving off gaseous formaldehyde which reacts with ammonia gasses released by said faeces forming a slow-release nitrogen fertilizer.

U.S. Pat. No. 3,826,638 discloses a method of preparing fertilizer from manure, the method comprising mixing wet manure, polyalkaline amine, and an aldehyde, and drying to prolong the time length of potentially available nitrogen, preferably the polyalkaline amine is polyethylenimine or polyethylene polyamine, and the aldehyde is formaldehyde.

GB 1 483 150 discloses a method of treating human and animal waste products in the form of slurry to produce a semi-solid product, the method comprising an aldehyde and a nitrogenous substance capable of complexing with said aldehyde and adjusting pH to less than 4, preferably formaldehyde and urea are used, thereby obtaining a controlled release fertilizer which is sterile and odourless.

SUMMARY OF THE INVENTION

In an aspect, it is the object of the present invention to seek to provide an improved method and apparatus for disposing waste matter from animals, in particular from farm animals.

In another aspect, it is the object of the present invention to seek to provide an improved method and apparatus to retain nitrogen in waste matter from animals.

In a further aspect, it is the object of the present invention to seek to provide an improved method and apparatus to reduce or to avoid loss of ammonia from waste matter from animals.

In still a further aspect, it is the object of the present invention to seek to provide alternative use of animal waste matter than agricultural disposal.

In still a further aspect, it is the object of the present invention to seek to provide an improved method and apparatus for producing biogas fuel from waste matter from animals.

In still a further aspect, it is the object of the present invention to seek to provide an improved method and apparatus for producing urea from waste matter from animals.

Further objects appear from the description elsewhere.

Solution

Method

In an aspect, these objects are fulfilled according to the invention by providing a method of treating waste matter from animals, the method comprising:

a) collecting waste matter from the animals;

b) inhibiting urease activity in said collected waste matter; and c) separating said urease-activity inhibited waste matter into a urea-rich fraction and a urea-lean fraction;

whereby is obtained that the waste matter is separated into a urea-rich fraction, which in a preferred embodiment essentially consists of a liquid fraction comprising urea and other components soluble in liquid manure, and into a urea-lean fraction, which in a preferred embodiment essentially consists of a solid fraction, and/or slurry fraction comprising solid faeces, for both of which fractions urease-catalytic activity on the hydrolysis of urea has been inhibited. Consequently, both said urea-rich fraction and said urea-lean fraction could be further processed without hydrolysis or only insignificant hydrolysis of urea into ammonia and carbon dioxide whereby it is ensured that loss of urea due to hydrolysis is limited and that production of ammonia which is considered an unpleasant odorant is reduced.

Further, the urease-inhibited urea-rich fraction is a particularly useful animal waste matter urea product. It can be used as a raw material for producing various urea products e.g. urea formaldehyde plastic, barbiturates, and melamine, etc., and applied as animal fodder, moisture lotion agent, binder agent, snow- and de-icing agent, agent for separation fatty acids, cleaning of smoke gasses, paper coating, chipboard binder component. This is a particular advantage for the farmer who can produce exactly the number of livestock that he wishes without running the risk straining the environment by disposing the waste matter through the agricultural system. He can dispose the liquid manure in form of useful products, e.g. urea formaldehyde plastic products thereby avoiding excess manuring with ammonia, nitrite and phosphate, and other components of liquid manure.

A further advantage of the method according to the invention is that only a minimum of ammonia is produced in stable systems due to hydrolysis of urea whereby an improved indoor climate in the stables can be obtained. This improved indoor climate results in an increased lung capacity of the stocked animals, i.e. an improved heath condition of the animals and consequently a more effective breeding of livestock can be obtained. Further, since there is a minimum emission of ammonia from the stable systems, pollution of the atmosphere with ammonia and its associated environmental problems can be reduced or eliminated.

A still further advantage of the method is that the urease-inhibited urea-lean fraction is a particularly useful biogas fuel as a fuel for production of biogases, e.g. methane. Because of the low content of urea, which is a major source of ammonia in biogas fuels, and because of the inhibition of urease catalytic activity on hydrolysis of urea, little or no ammonia is present or produced in the urea-lean fraction. Consequently, distillation or rectification columns for the required separation of ammonia in prior art biogas plants are not required for biogas plants based on fuels of the urease-inhibited urea-lean fraction of waste matter according to the present invention. Also, separation of other components such as phosphate is not required or can be significantly simplified for such biogas plants whereby large costs of equipment can be avoided.

Animal Waste Matter Treatment System

In another aspect these objects are fulfilled by a system for treating waste matter from animals, the system comprising:

g) a waste-matter collection means, said collection means being adapted to collect waste matter from the animals;

h) at least one separating means, said separating means being adapted to separate said collected waste matter into a urea-rich fraction and a urea-lean fraction; and at least one urease-inhibitor supply means; said supply means being adapted to supply at least one urease inhibitor to said collected waste-mater, said urea-lean fraction, and/or said urea-rich fraction;

whereby it is obtained that the advantages mentioned for the method according to the invention can accomplished.

Urea-Lean Biogas Fuel Product

In still another aspect these objects are fulfilled by providing a urea-lean biogas fuel product, the product comprising a urea-lean fraction of waste matter from animals wherein the waste matter has been treated by a method according to the invention, or wherein the waste matter has been treated in a waste-matter treatment system according to the invention whereby it is obtained that waste matter can be converted into a useful product for the preparation of environmentally friendly urea-lean biogas fuel product.

Urea-Rich Animal Waste-Matter Product

In still another aspect these objects are fulfilled by providing a urea-rich animal waste-matter product, the product comprising urea produced from a urea-rich fraction of waste matter from animals wherein the waste matter has been treated by a method according to the invention, or wherein the waste matter has been treated in a waste-matter treatment system according to the invention whereby it is obtained that waste matter can be converted into a useful starting material or raw material for production of chemicals, such as urea formaldehyde.

Controlling Nitrogen Content of Animal Manure

In still another aspect these objects are fulfilled by providing a method of controlling the content of nitrogen in manure from animals wherein the manure is treated by a method according to the invention, or wherein the manure is treated in a waste-matter treatment system according to the invention whereby a major component of manure can be controlled.

Reducing Gaseous Ammonia in Stables

In still another aspect these objects are fulfilled by providing a method of reducing gaseous ammonia in stables for animals, the method comprising controlling the content of nitrogen in manure from the animals by a method according to the invention whereby a healthy ammonia-free or ammonia-reduced indoor climate can be established for the animals.

Stable Comprising Animal Waste-Matter Treatment System

In still another aspect these objects are fulfilled by providing a stable for animals, the stable comprising a system for treating waste-matter according to the invention whereby stocking of livestock can be obtained including facilities for treating waste matter such as manure from the animals.

Generally, a stable system is defined as all mechanical parts and devices used in breeding and storage of livestock, and all mechanical parts and devices used to discharge, store, and transport faeces and liquid manure of the livestock.

Biogas Reactor System

In still another aspect these objects are fulfilled by providing a biogas reactor system for producing biogas from waste matter from animals, the system comprising a waste-matter treatment system according to the invention whereby a biogas fuel with a very low content of urea, optionally urease-inhibited biogas fuel, is obtained which ensures that the level of ammonia and ammonium can be kept sufficient low for the biogas reactor system to operate, or to operate sufficiently efficient without requiring additional ammonia/ammonium-stripping. Consequently, a very costly ammonia/ammonium-stripper unit of the biogas reactor system can be avoided. Typically for an anaerobic operated biogas reactor system the level of ammonia and ammonium should be kept below 0.01 M total ammonia/ammonium for the biological decomposition activity not to be adversely affected. Generally, however, the acceptable level of ammonia/ammonium depends on the biogas reactor micro organisms (e.g. Methanosarcina, Methanothrix, and Methanobacterium) as well as the level of nutrients, e.g. salts (e.g. generally with an increasing degree of inhibition on the decomposition along the series: calcium, magnesium, sodium, potassium, and ammonium).

Further, a large amount of salt components, e.g. salt components of liquid manure of the animal waste matter are removed from the urea-lean fraction whereby it is obtained that the biogas fuel does not contain these components either. Thereby, the influence on decomposition-inhibition by waste-matter salts on the biogas fuel can be reduced, and additional separation units in the biogas reactor system for these salt components can be avoided.

It should be noted that the biogas reactor system does not need to have the waste-matter treatment system according to the invention installed on the biogas reactor site. The biogas fuel can be produced at a separate site, e.g. at a pig or cattle farmer's site far from the biogas reactor, and then be transported to the biogas reactor system for it decomposition, and eventual use.

Production of Urea from Animal Waste Matter

In still another aspect these objects are fulfilled by providing a method of producing urea from waste matter of animals, the method comprising:
a) producing a urea-rich fraction of the waste matter from the animals by a method comprising:
  i. collecting waste matter from the animals;
  ii. inhibiting urease activity in said collected waste matter; and
  iii. separating said urease-activity inhibited waste matter into a urea-rich fraction and a urea-lean fraction; and
b) separating urea from said urea-rich fraction;
whereby waste matter from animals, in particular waste matter comprising faeces and liquid manure from farm animals, can be turned into a useful urea product.

Production of Urea Formaldehyde

In still another aspect these objects are fulfilled by providing a method of producing urea formaldehyde, the method comprising:
a) producing urea from waste matter from animals according to the invention; and
b) reacting said urea with methanal;
whereby waste matter from animals, in particular waste matter comprising faeces and liquid manure from farm animals, can be turned into a useful urea formaldehyde product.

This method of producing urea is very different from present day's method. According to prior art methods urea, $CO(NH_2)_2$, also designated carbamide, is synthetically produced in industry by a reaction between ammonia, $NH_3$, and carbon dioxide, $CO_2$, according to the following reaction:

$$2NH_3 + CO_2 \rightarrow CO(NH_2)_2 + H_2O \quad (1)$$

Urea is a very important substance in the processing of plastics because its is able to react spontaneously, fast, and exothermally with methanal, HCHO, also designated formaldehyde, and polymerises with a catalytic acid according to the three reactions (2)-(4)

$$HCHO + CO(NH_2)_2 \rightarrow HOCH_2-NH-CO-NH_2 \quad (2)$$

wherein the reaction product is methylolurea which in turn reacts with methanal forming dimethylolurea $$HOCH_2-NH-CO-NH_2 + HCHO \rightarrow HOCH_2-NH-CO-NH-CH_2OH \quad (3)$$

which in turn reacts—in an excess of methanal —to a thermosetting resin designated urea formaldehyde $$dimethylolurea \rightarrow urea\ formaldehyde \quad (4)$$

In reaction equation (4) the product is designated urea formaldehyde because formaldehyde is the ordinary designation of methanal. Other designations for urea formaldehyde are carbamide resin and urea resin.

Urea formaldehyde is applied extensively in processing of wood articles as the substance constituting the binding agent, the adhesive, in chipboards and MDF-boards. It is estimated that about 90% of wood adhesives on the world market are based on urea formaldehyde—yet based on synthetically produced urea.

This means that today the thermosetting urea formaldehyde is produced based on synthetically produced urea. But the chemical properties of urea do not depend on how it was made. Consequently, the synthesis of urea formaldehyde could in principle just as well be based on animally produced urea as on synthetically produced urea. This means that in principle the production of urea formaldehyde could be based on liquid manure, naturally produced in commercial application of livestock. The reason that urea formaldehyde is not produce based on animal waste matter today is because urea decomposes—hydrolysed to carbon dioxide and ammonia—when it gets into contact with faeces of the livestock in the stable systems. If the farmer could avoid the decomposition of urea into carbon dioxide and ammonia in the manure/liquid manure it would be possible—applying known chemical engineering units—to recover urea, and later process it into urea formaldehyde. At the same time the farmer could also convert the environmental problem of excess maturing to a new commercial business area, production of plastics based on animal waste matter.

In the attempt to identify a process for converting urea of livestock to urea formaldehyde one has to understand why the manure contains only the decomposition products—typically ammonia—and depending on pH—ammonium. Whereas a chemical manufacturer would consider the equation (1) for the production of urea, a farmer would consider the metabolism of proteins in the organisms of the livestock. In this metabolism, the proteins—from the feed are converted into amino acids which are absorbed by the animal organism through the intestines. These absorbed amino acids participate in various essential biochemical relations in the organism, the ammonia being a poisonous waste product. In some animals for example in pigs, but also in human beings, this poison is converted to urea and glutamine, both being eliminated in the kidneys. For example, in human beings it is estimated that 60-75% of the urea substance is eliminated in the kidneys, the rest being eliminated in the intestines. Yet in the intestines the urea substance gets into contact with the enzyme urease which under alkaline conditions catalyses the hydrolysis of urea, the carbamide hydrolysis, defined by $$CO(NH_2)_2 + H_2O \rightarrow 2NH_3 + CO_2 \quad (5)$$

The presence of this enzyme is caused by the presence in the intestines of cultures of bacteria comprising or producing urease. It should be noted that the ammonia product from the hydrolysis is reabsorbed into the intestines from the organism—under normal conditions—and so nearly all ammonia is eliminated in form of urea in the kidneys.

In this respect, the problem is that faeces and liquid manure are mixed in the stable system; 30% by weight of dry faeces are bacteria, including micro organisms comprising or producing urease too, which bacteria result in hydrolysis of urea according to the reaction equation (5). Associated with equation (5) there is a phase transition

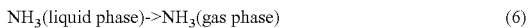
$$NH_3(\text{liquid phase}) \rightarrow NH_3(\text{gas phase}) \qquad (6)$$

whereby the stables exhibit strong (smelling) ammonia vapours which additionally pollute the atmosphere—both indoor and outdoor of the stables. A deteriorated indoor atmosphere (climate)—in this case an increased partial pressure of ammonia, the lung capacity of the livestock is decreased and consequently, the livestock will grow more slowly; by constant feeding dose the livestock productions is decreased by increasing partial pressure of ammonia in the stables.

Producing Biogas Fuel from Animal Waste Matter

In still another aspect these objects are fulfilled by providing a method of producing biogas fuel from waste matter of animals, the method comprising:

a) producing a urea-lean fraction of the waste matter from the animals by a method comprising:
  i. collecting waste matter from the animals;
  ii. inhibiting urease activity in said collected waste matter; and
  iii. separating said urease-activity inhibited waste matter into a urea-rich fraction and a urea-lean fraction; and
b) optionally drying said urea-lean fraction;

whereby waste matter from animals, in particular waste matter comprising faeces and liquid manure from farm animals, can be turned into a useful biogas fuel product.

PREFERRED EMBODIMENTS

Collecting Waste Matter

Generally, according to the invention the method comprises a) collecting waste matter from the animals whereby the waste matter to be treated is provided for processing.

Collection of waste matter from animals can be carried out in any suitable way known in the art. Preferably, waste matter is collected when the animals are concentrated in locations for their tending, e.g. for feeding, for drinking, and/or for yielding milk, or when they are concentrated in locations for transportation, or for retention before slaughtering. Other locations include locations where the conditions for producing waste matter are good, or locations where such waste-matter producing conditions could be made to stimulate the animals to urinate or defecate.

Preferably collection of waste matter takes place in stables where the animals are stocked. However, collection of waste matter can take place in the free as well, e.g. at locations where free going animals are stocked for their transportation to slaughterhouses.

Known waste matter collections facilities comprise stables wherein the animals are located and tended. Below the stables are stable basements wherein waste matter, e.g. liquid manure, faeces, litter, and other matter disposed from the animals are collected. Stable floors through which said waste matter is guided for collection and storage, detach the stables and stable basements.

Urease-Activity Inhibiting Treatment

Generally, according to the invention, the method comprises (b) inhibiting urease activity in said collected waste matter whereby it is obtained that urease-catalyzed hydrolysis of urea to ammonia is inhibited, either reversibly or irreversibly, and that loss of nitrogen and/or production of ammonia from the waste matter is substantially reduced or avoided. Consequently, the unpleasant odour and unhealthy condition due to ammonia in the stables can be reduced or avoided.

Generally, it is known to inhibit the catalytic activity of urease on hydrolysis of urea, either by removing water so that hydrolysis cannot take place, or by inhibiting the active site of urease as such. Known methods comprise addition of inhibitors as cited e.g. in the referenced prior art, such as U.S. Pat. No. 3,565,599, heat treatment, and irradiation with ionizing radiation. Generally, the method of inhibiting urease activity in said collected waste matter depends on the intended use of the urease-inhibited waste matter.

Thus, for example for urease-inhibited waste matter used in the preparation of a fertilizer to be used for disposing waster matter through the agricultural system, the urease-inhibited waste matter should be compatible with components of the prepared fertilizer. Also, urease-inhibited waste matter should not adversely affect the environment where the fertilizer is applied.

Also, for application of urease-inhibited waste matter as a raw material in production of chemicals, the applied urease-activity inhibitor should be compatible used reagents and not interfere with or adversely affect neither the production nor the intended use of such chemicals.

Consequently, the selection of method of inhibition of urease activity generally depends on the application.

Accordingly, in a preferred embodiment said inhibition comprises: reversible inhibiting urease activity, irreversibly inhibiting urease activity, and/or a combination thereof whereby it is obtained that the urease inhibition can either be applied for a period wherein reversible inhibition conditions apply, or for a longer period wherein irreversible inhibition conditions apply.

Reversible inhibition conditions include conditions of temporarily different pH, e.g. buffering about isoelectric point of urease about pH 5.5, temperature, or pressure, or presence of a reversible inhibitor component. After a reversible inhibition period, the inhibition condition can be returned to its previous state of no or substantially no inhibition of the urease catalytic activity. Reversible inhibition can be applied to both the urea-rich and the urea-lean fractions.

Irreversible inhibition conditions include conditions of permanent or essentially permanent inhibition of the urease catalytic activity. Irreversible inhibition can be applied to both the urea-rich and the urea-lean fractions.

Also, a combination of reversible and irreversible inhibition of urease activity can be applied whereby e.g. the urea-rich fraction can be irreversibly urease-activity inhibited, and the urea-lean fraction can be reversible urease-activity inhibited, either competitively by substrates competing for binding to the active site, or non-competitively by substrates binding to other parts of the urease than the active binding site to thereby alter the confirmation of the urease so that reversible inactivation of the catalytic site results. This is particularly advantageous for applications wherein the urea-lean fraction does not require addition of an irreversible inhibitor and/or wherein an additional separation step for removing an irreversible inhibitor from the urea-lean fraction before its further processing can be avoided.

In a preferred embodiment said inhibition comprises reversible inhibiting urease activity of said collected waste matter before said separation of said urease-activity inhibited waste matter into a urea-rich fraction and a urea-lean fraction whereby it is obtained that reversible inhibition of urease activity is obtained for a sufficiently long time to separate the urease-activity inhibited waste matter into a urea-rich fraction and a urea-lean fraction. Then the urea-rich fraction can be treated to irreversibly inhibit the urease-catalytic activity whereas the urea-lean fraction need not. For many applications of the urea-lean fraction, the amount of urea and the amount of water for the hydrolysis of urea are so low that only insignificant hydrolysis takes place.

Reversible Urease-Activity Inhibition

According to the invention the method comprises b) inhibiting urease activity in said collected waste matter whereby it is obtained that hydrolysis of urea is not catalyzed by urease, as long as the urease activity is inhibited. During such a urease-activity inhibited period, waste matter can be stored or processed without urease-catalysed hydrolysis of urea whereby loss of nitrogen and/or generation of ammonia can be avoided.

In a preferred embodiment, said inhibition comprises a reversible inhibition of urease activity comprising treating said collected waste matter, said urea-rich fraction, or both, by a method comprising: decreasing and/or increasing pH; buffering pH; decreasing and/or increasing temperature; decreasing and/or increasing pressure; decreasing and/or increasing ionic strength, or a combination thereof said urease-activity is inhibited reversibly whereby the duration of the urease inhibition can be controlled. This is particularly advantageous for the initial phase of the processing of the collected waste matter wherein the reversible inhibition period may last for a sufficiently long time for storage and separation of the treated waste matter into a urea-rich fraction and a urea-lean fraction, respectively, before the urease activity returns to an active state. Since the urea-lean fraction is lean in urea, the urea conversion is low when the urease activity returns. In the urea-rich fraction, however, the urea conversion could have been high if the urease activity was allowed to return. However, this can be avoided, preferably by subjecting the urea-rich fraction to a further eversible or irreversible urease-activity inhibition treatment (see below).

Irreversible Urease-Activity Inhibition

According to a preferred b) inhibiting urease activity in said collected waste matter comprises irreversible inhibition whereby it is obtained that the time period of inhibition of the urease activity is extended to a very long period, preferably irreversibly, but in practice limited e.g. by the lifetime of the inhibitor. Further, the type and amounts of the components that the reversible inhibition treatment introduces into the waste matter can be controlled.

1. According to a preferred embodiment said inhibition comprises a irreversible inhibition of urease activity comprising treating said collected waste matter, said urea-rich fraction, or both, with an irreversible inhibitor, said inhibitor being selected among the group comprising:

urea compounds such as hydroxyurea, selenourea, phenylurea, thiourea;

hydroxamates such as amino acid hydroxamates, acetohydroxa-mate;

benzoeates such as p-substituted mercuribenzoate, p-chloromercuribenzoate, p-hydroxymercuribenzoate, iodosobenzoate;

sulfonates such as p-chloromercuribenzenesulfonate;

imides such as N-ethylmaleimide;

phosphor compounds such as phosphoramidate, phosphate;

monovalent ions such as $F^-$, $Na^+$, and $K^+$;

divalent metal ions such as $Hg^{2+}$, $Cu^{2+}$, $Fe^{2+}$, $Co^{2+}$, $Zn^{2+}$, $Ni^{2+}$, $Mn^{2+}$, $Cd^{2+}$, $Ag^+$, $Mg^{2+}$ (weak), $Ba^{2+}$, preferably $Cu^{2+}$, $Ag^+$, or $Pb^{2+}$, or a combination thereof in form of at least one water-soluble salt, and/or at least one electrochemically-released ion;

trivalent ions such as $As^{3+}$; and at least one nickel-complexing agent, preferably dimethylglyoxime, ethylenediamine, EDTA, or a combination thereof, and other compounds such as beta-mercaptoethanol, iodine, suramin, phenylsulfinate, and furacin, whereby it is obtained that hydrolysis of urea is not catalyzed by inhibited urease. Consequently, the irreversibly urease-activity inhibited urea-rich fraction can be stored or processed without urease-catalysed conversion of urea whereby loss of nitrogen and/or generation of ammonia can be avoided. This is particularly advantageous for long storage periods of the urea-rich fraction before it is subjected to a subsequent treatment. Another advantage is that once the urease activity is irreversibly inhibited, the urease cannot function to catalyse the hydrolysis of urea to ammonia.

Reversible and Irreversible Urease-Activity Inhibition

According to a preferred embodiment the method comprises:

a) reversibly inhibiting urease activity in said collected waste matter;

b) separating said reversibly urease-activity inhibited waste matter into a urea-rich fraction and a urea-lean fraction; and c) irreversibly inhibiting urease activity in said urea-rich fraction whereby it is obtained that hydrolysis of urea is not catalyzed by urease in the urea-rich fraction, or is only catalysed by urease to a limited extend, and that hydrolysis of urea is only catalysed by urease in the urea-lean fraction to the extend residual urea is present, water for the hydrolysis is present, and separated urease has returned to its active state. Since the urea-lean fraction can be dried hydrolysis can essentially be avoided.

Separation Into Urea-Lean and Urea-Rich Fractions

According to the invention the method comprises c) separating said urease-activity inhibited waste matter into a urea-rich fraction and a urea-lean fraction whereby it is obtained that the waste matter is separated into an urea-rich fraction containing a major amount of the total amount of urea and an urea-lean fraction containing little or no urea. Consequently, the waste matter is separated into a urea-lean fraction wherein the content of urea is low and thus the urease-catalysed hydrolysis of urea is low. In the urea-rich fraction, however, the content of urea is high, and the urease-catalysing hydrolysis of urea could be high if it were not inhibited.

In an embodiment, c) separating said urease-activity inhibited waste matter into a urea-rich fraction and a urea-lean fraction is accomplished by sedimentation of solids whereby said solids make up the urea-lean fraction and the liquid fraction makes up the urea-rich fraction. The liquid fraction is removed by any suitable method, e.g. by surface layer pumping or by decantation. Preferably sedimentation is accomplished by centrifugation whereby the sedimentation process can become accelerated and the time for separating the urea-rich fraction and the urea-lean fraction can be controlled and accomplished in time before return of the urease activity. In particular it is preferred that the sedimentation is carried out so that substantially the entire liquid fraction has become separated from the solid fraction, e.g. by application of heat.

The time of return of urease-activity is particularly important for the urea-rich fraction. It is preferred that the reversible inhibition time is selected to be sufficiently long for the urea-rich fraction to be subjected to yet another reversible urease-inhibition treatment or subjected to an irreversible urease inhibition.

Urea-Lean Fraction

In preferred embodiments said inhibition comprises reversible inhibiting urease activity of said collected waste matter before said separation of said urease-activity inhibited waste matter into a urea-rich fraction and a urea-lean fraction whereby it is ensured that the lean-urea fraction is in a suitable form for its further processing. A liquid urea-lean fraction can easily be pumped through conduits for its subsequent treatment, e.g. for preparation of a biogas fuel for biogas incinerators. A solid urea-lean fraction can easily be conveyed by conveyer belts for its subsequent treatment, e.g. for preparation of a solid urea-lean fertilizer.

Urea-Rich Fraction

Generally, said urea-rich fraction is in any suitable form for its further processing.

In preferred embodiments said urea-rich fraction is a liquid, a solid or combination thereof. A liquid urea-rich fraction can easily be pumped through conduits for its subsequent treatment, e.g. for preparation of a animal waste matter urea product. A solid urea-rich fraction can easily be conveyed by conveyer belts for its subsequent treatment, e.g. for preparation of melamine or barbiturates, etc. as mentioned above.

Besides having large amount of urea, the urea-rich fraction comprises a number of animal-specific and feeding-specific characteristic substances the amounts and relative amounts of which can be applied as origin-indicators of the urea-rich fraction.

Typical ranges of organic substances in 500 ml/d of urine of young pigs having a pH in the range 4.5-8.2 and a dry mass of 50-72 g/d are shown in Table 1.

TABLE 1 organic substances in pig urine

| Organic substances | Amount | Unit |
|---|---|---|
| Urea | 200-1270 | mmol/d |
| Creatine | 0.397-0.702 | mmol/d |
| Guanidine | 2.0-6.4 | µmol/d |
| Methylguanidine | 8-30 | µmol/d |
| Guanidinoacetic acid | 88-382 | µmol/d |
| Guanidinosuccinic acid | 29.7-87.9 | µmol/d |
| Alanine | 173-507 | µmol/d |
| Arginine | 12.7-47.7 | µmol/d |
| Carnosine | 11.8-94.6 | µmol/d |
| Citrulline | 4.0-29.6 | µmol/d |
| Glycine | 801-1999 | µmol/d |
| Histidine | 785-1795 | µmol/d |
| Isoleucine | 12.4-42.8 | µmol/d |
| Leucine | 26.1-69.5 | µmol/d |
| Lysine | 77-907 | µmol/d |
| Methionine | 5.1-34.7 | µmol/d |
| Ornithine | 24.9-69.5 | µmol/d |
| Phenylalanine | 39.8-96.8 | µmol/d |
| Serine | 251-667 | µmol/d |
| Threonine | 127-421 | µmol/d |
| Tyrosine | 64.3-203.7 | µmol/d |
| Valine | 31.1-62.3 | µmol/d |
| Choline | 11-433 | µmol/d |
| Carnitine | 298-418 | µmol/d |
| Ethanolamine | 331-567 | µmol/d |
| o-Phosphoethanolamine | 94-156 | µmol/d |
| Methylamine | 0.15-0.19 | µmol/d |
| Dimethylamine | 0.34-0.43 | µmol/d |

TABLE 1-continued organic substances in pig urine

| Organic substances | Amount | Unit |
|---|---|---|
| Piperidine | 55-83 | µmol/d |
| Spermidine | 14-20 | µmol/d |
| Spermine | 1-3 | µmol/d |
| Putrescine | 21-35 | µmol/d |
| p-Aminobenzoic acid | 2.3-9.6 | µmol/d |
| o-Aminobenzoic acid | 2.3-16.3 | µmol/d |
| p-Tyramine | 3.6-12 | µmol/d |
| Dopamine | 1.01-2.44 | µmol/d |
| 3-Methoxytyramine | 0.18-1.05 | µmol/d |

TABLE 2 inorganic substances in pig urine

| Inorganic substances | Amount | Unit |
|---|---|---|
| Chloride | 80-270 | mmol/d |
| Phosphate | 1-20 | mmol/d |
| Pyrophosphate | 2-38.9 | µmol/d |
| Inorganic sulfate S | 33-41 | mmol/d |
| Sulfuric acid ester S | 2.5-34.4 | mmol/d |
| $SO_4^{2-}$ | 12-42 | mmol/d |
| Thiocyanate | 0.01-0.1 | mmol/d |
| Cyanide | 0.08-0.23 | µmol/d |
| Flouride | 47-153 | µmol/d |
| Bromide | 20-84 | µmol/d |
| Iodide | 0.41-3.81 | µmol/d |
| Boron | 9-90 | µmol/d |
| Potassium | 40-100 | mmol/d |
| Calcium | 4.54-5.94 | mmol/d |
| Sodium | 80-560 | mmol/d |
| Magnesium | 2.5-8.3 | mmol/d |
| Iron | 0.22-6.3 | µmol/d |
| Copper | 0.06-1.81 | µmol/d |
| Zinc | 2.1-18 | µmol/d |
| Arsenic | 0.05-8.1 | µmol/d |

Definition of Terms, and Expressions

Within the present context it is intended that the expression "waste matter" designates matter discharged from the body of an animal, in particular a farm animal such as pig, cow, sheep, etc. In the present context the term animal is also intended to include humans. Waste matter comprises liquid excrete, e.g. urine secreted by the kidneys of the animals. It is rich in end-products of protein metabolism such as urea together with salts and pigments. Further it includes solid excrete, e.g. faeces discharged from the alimentary channel through the anus of the animal.

Within the present context it is intended that the expression "inhibiting urease activity" designate the action or the result of restraining the activity or functioning of urease in catalyzing hydrolysis of urea to carbon dioxide and ammonia in an aqueous environment.

The expression "reversibly inhibiting urease activity" designates inhibition of urease activity under conditions of competitive binding to the active site of competing substances, or non-competitive binding of substances to non-active sites which alters the conformity of the urease and eventually inactivates the active site reversibly, both for which the urease activity is able to return to its previous active state when the conditions are reversed. For example, within the sensitive pH range of the urease activity (6-8), lowering pH temporarily results in a decreased urease activity. However, by returning pH to its previous level, the urease activity increases, albeit not necessarily to its former level of activity.

The expression "irreversibly inhibiting urease activity" designates inhibition of urease activity under conditions that are substantially irreversible and/or conditions that cannot be reversed, e.g. if the nature of functional group at the active site and the mechanism of the catalytic activity are destroyed. For example, decomposition of urease and selectively blocking of active centers that are responsible for the catalytic effect of urease will result in substantially irreversible inhibition of urease activity. Such irreversible conditions can be obtained by e.g. covalently bonding of protecting groups such as nickel (II).

BRIEF DESCRIPTION OF DRAWINGS

In the following, by way of examples only, the invention is further disclosed with detailed description of preferred embodiments. Reference is made to the drawings in which.

DESCRIPTION OF A PREFERRED EMBODIMENT

Figure 1:
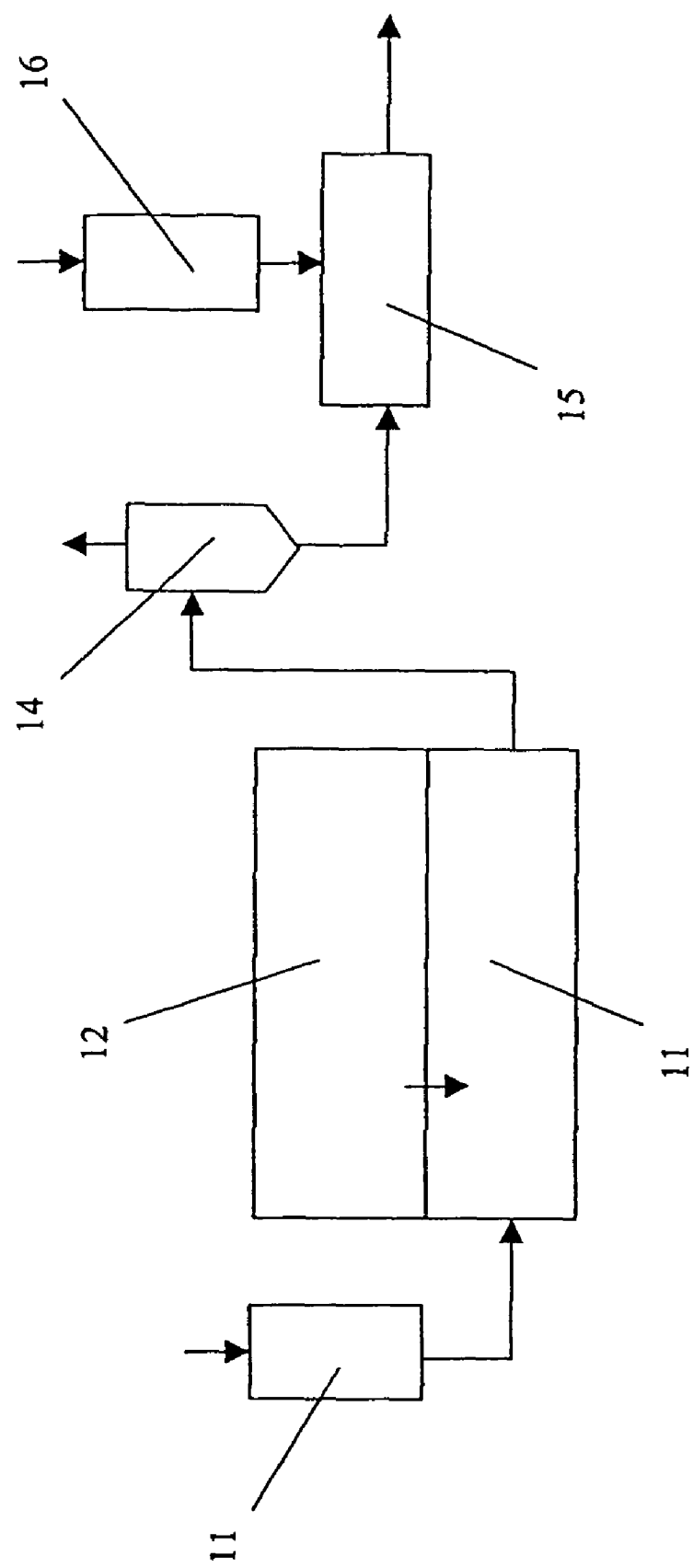
FIG. 1 shows a sketch of an embodiment of the present invention illustrating an exemplary system for treating waste matter from animals in a stable.

FIG. 1 shows a sketch of an embodiment of the present invention illustrating an exemplary system for treating waste matter from animals in a stable. A first urease-inhibitor storage tank 11 supplies urease-inhibitor to a lower stable 13 located below an upper stable 12 for accommodating the animals. The lower stable is connected to a separation means 14 for separating the inhibitor-treated waste matter into a urea-rich fraction and urea-lean fraction, here a decantation centrifuge. The urea-rich fraction is connected to a storage container 15.

Animal waste matter, here in form of manure and liquid manure, is collected from the animals, here pigs or cattle, in the upper stable 12 and transferred to the lower stable. The lower stable preferably contains a liquid residue comprising urease inhibitor from a previous collection, or contains water containing urease inhibitor. Optionally, animal waste matter from the upper stable is flushed into the lower stable using water containing urease inhibitor. Since the waste matter is brought into contact with a urease inhibitor, the production of ammonia through urease-catalyzed hydrolysis of urea is limited whereby the production of ammonia and subsequently the smell of ammonia are reduced.

The number of animals in the upper stable determines the amount of manure, both faeces and urine, in terms of volume per time unit supplied to the lower stable.

The urease-inhibited collected waste matter is subjected to a separation into a urea-rich and urea-lean fraction respectively in a decantation centrifuge 14.

The urea-lean fraction is stored in a separate storage container (not shown) for later disposal, or it is transferred to a biogas reactor system for use as a urea-lean biogas fuel in production of biogas.

The urea-rich fraction is stored in a urea-rich fraction storage tank 15 for later disposal or later transport to further processing, or it is transferred to a urea-treatment system for the production of urea. In a preferred embodiment, the storage tank 16 is supplied by a urease inhibitor from a second urease-inhibitor container 16 for additional inhibition of the urease-catalytic activity on hydrolysis of urea. In a preferred embodiment, the second urease-inhibitor comprises an irreversible urease-inhibitor, e.g. $Cu^{2+}$. Alternatively, in case the irreversible urease-inhibitor comprises a metal this could be supplied by electrochemical oxidation processes.

Figure 2:
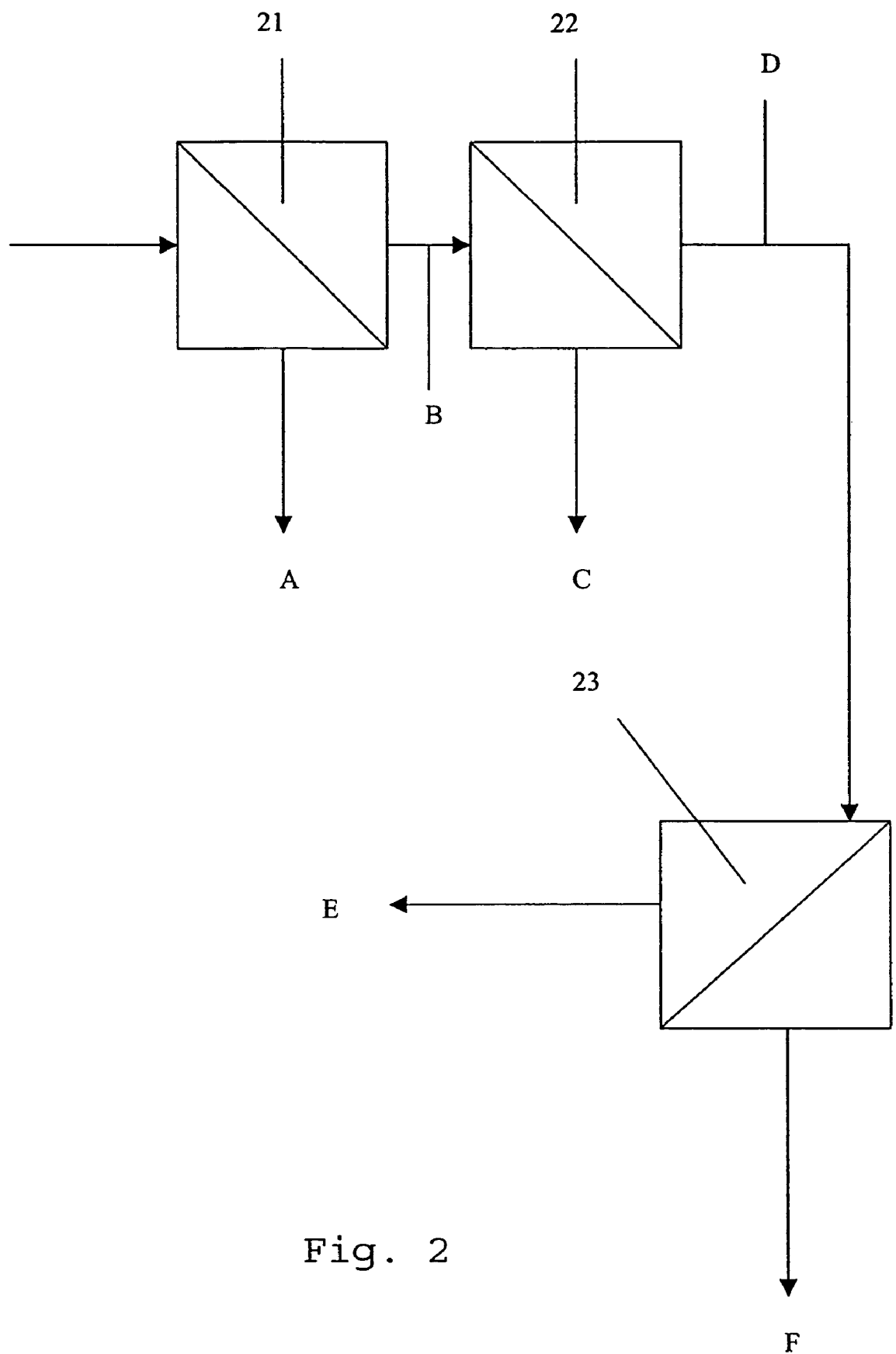
FIG. 2 shows a sketch of an embodiment of a system comprising units for treating and concentrating urea in a urea-rich liquid.

FIG. 2 shows a sketch of an embodiment of a system comprising units for treating and concentrating urea in a urea-rich liquid suitable for processing the urea-rich fraction from waste matter of animals according to the invention.

Processing of the urease-inhibited urea-rich fraction of animal waste matter comprises chemical operations for preparing the urea product for its application.

Generally, the urea-rich fraction processing comprises storage in a temporary storage tank, e.g. a separate storage tank (not shown) at the processing site, or e.g. the storage tank 15 if the processing units are not located at the stable site, whereby accumulation of suitable amounts and storage for a convenient point in time for economical further processing can be obtained.

Generally separations comprise separations of litter such as various cellulose fibers, sand, etc. by suitable filtration means (not shown) whereby large variability of decantation efficiency at the farmers' sites can be reduced before further processing. Optionally, discarded residues can be recycled to the irreversible urease-inhibitor storage container, or optionally irreversible urease inhibitor can be recovered and recycled.

Preferably the urea-rich fraction processing comprises ultra-filtration in an ultra-filtration unit 21 whereby microorganisms and macromolecular substances such as urease and bilirubin can be removed in a reject A. This improves the urea-rich product with respect to avoid fouling and scaling of filtration membranes in optional subsequent filtering processes. For some applications, the urea-rich fraction can be used in this form.

Preferably, however, the permeate B comprising water, urea, amino acids, and inorganic salts of the ultra-filtered urea-rich fraction is further subjected to a nano-filtering process in a nano-filtration unit 22 whereby further components such as irreversible inhibitors such as divalent ions of copper, silver, lead or nickel, monovalent ions, complexing agents and further components, if not already removed, e.g. liquid manure components such as urease, bilirubin and its derivatives, are removed C. At this stage the urea-rich fraction D can be used as a urea product for use e.g. as a de-icing agent.

In a still further embodiment, permeate D comprising water, urea, and monovalent ions of the urea-rich fraction is further subjected to a hyper filtration process (e.g. by inverse osmosis) in a hyper filtration unit 23 whereby water can be removed in a reject E and the urea-rich fraction can be concentrated into a urea concentrate F containing urea and additional ions such as sodium, potassium, calcium, phosphate, chloride, and creatinine.

Figure 3:
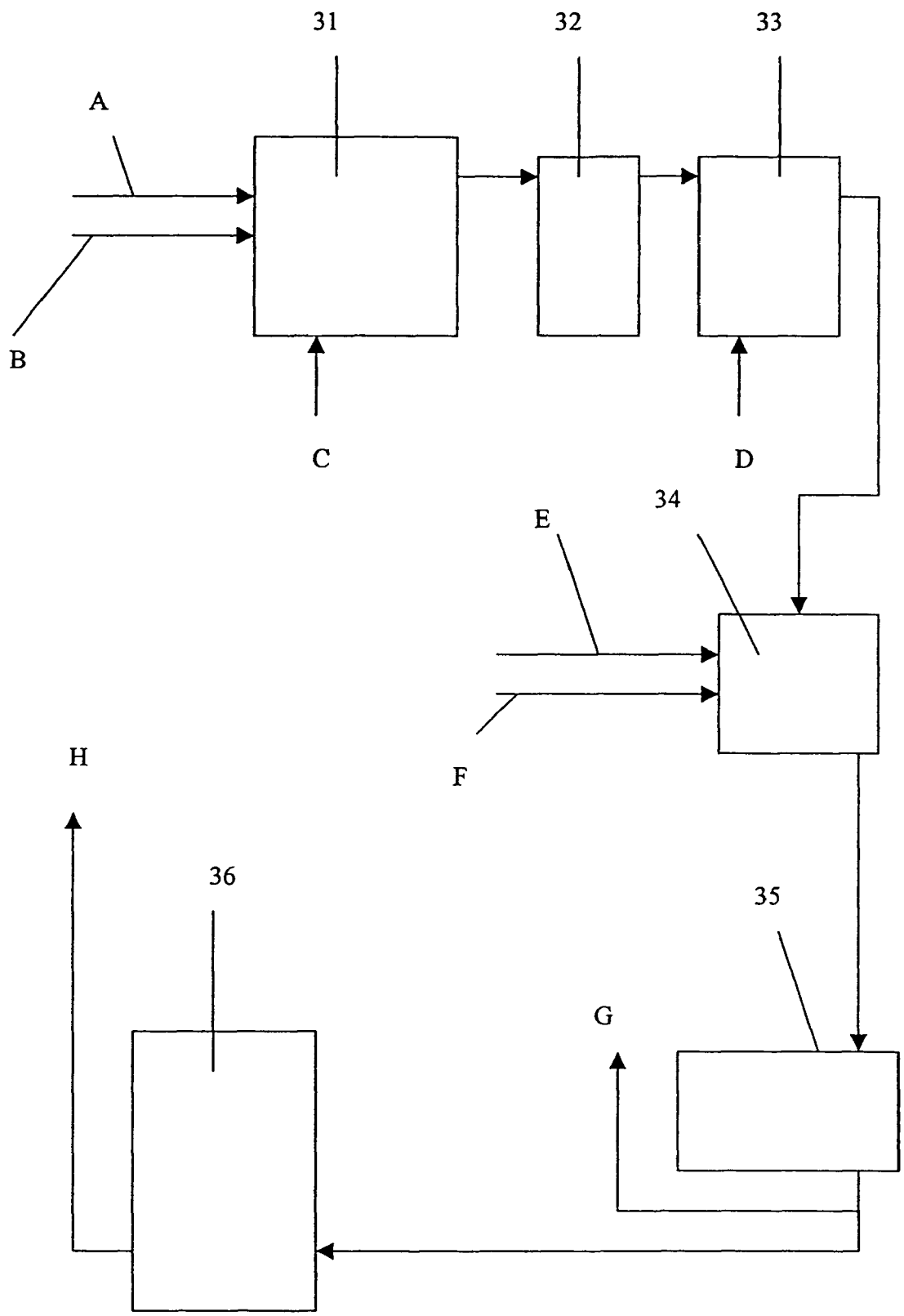
FIG. 3 shows a sketch of an embodiment of a system comprising units for polymerization of urea formaldehyde from a urea concentrate.

FIG. 3 shows a sketch of an embodiment of a system comprising units for polymerization of urea formaldehyde from a urea concentrate.

Urea concentrate A, methanal (formaldehyde) B and base C providing a pH including the range 8-9, but not an ammonium-based base, are conducted to a continuous stirred reactor 31. Instead of methanal a suitable precursor for methanal can be used, e.g. formalin, or water-free paraformaldehyde. The choice of paraformaldehyde would allow less water to be removed in the pre-concentration stage of the urea-rich fraction of the animal waste matter treatment according to the invention. In the continuous stirred reactor 31 various derivatives of methylol are formed. They are stored in an intermediate storage tank 32 before being transferred to a polymerization reactor 33. Polymerization of urea formaldehyde is carried out by exothermic condensation and splitting off of water under weak acidic conditions provided by addition D of a non-halogen acid such as acetic acid at a pH including the range 4-5.

The polymerization reaction is stopped in a quenching tank 34 by addition of a quencher E such as synthetic urea, melamine and/or phenol under weak alkaline conditions in the pH range including 7.5-8 provided by a non-ammonium base F. Depending on the application of the formed urea formaldehyde plastic different quenching techniques e.g. weak basic, neutral, and weak acidic conditions are applied at three parallel reactors each equipped with suitable pH control units.

Optionally the quenched urea formaldehyde product can become concentrated, optionally in a crystalline form, through a further distillation in a distillation unit 35 using e.g. vacuum distillation and/or flash distillation. It should be noted that this product will comprise in addition to urea accumulations of various inorganic salts such as sodium, potassium, calcium, phosphorous, chloride, and creatinine, and minor or trace amounts of amino acids.

The resulting urea formaldehyde plastic is used for various purposes, e.g. as a wood binder/adhesive G when dissolved in water, or as a powder binder/adhesive H when in a dried form, e.g. after spray drying in a spray drying unit 36.

EXAMPLES

Example 1

Urease Decomposition of Urea to Ammonia and Carbon Dioxide

For this example, a colourless urea reference system is defined by the following mixture: in a conical flask 10 g of synthetic urea is diluted with water to 50 ml, three drops of the acid-base indicator phenolphthalein is added.

This reference system is stable—in the sense that hydrolysis of urea does not take place. The colour is constantly colourless, the reaction according to equation (5) does not run, and therefore the weak base ammonia is not produced; pH does not increase whereby the colour shift of phenolphthalein into red does not occur.

If the reference system is contaminated with 1 ml of the enzyme urease—EC 3.5.1.5, 540 units per ml—a spontaneous and fast colour shift into red accurs—ammonia is formed and urea is hydrolysed according to reaction equation (5). After further 60 min the urease-contaminated system strongly smells of ammonia.

It is seen that the addition of urease to a urinal system instantaneously decomposes urea to ammonia and carbon dioxide.

Example 2

Urease-containing Liquid Manure and Methanal cannot Form Urea Formaldehyde

Starting from our reference system as described in example 1 and adding 30 ml 24% of methanal by weight—this concentration, 24% by weight, is used in the following examples where methanal is dosed—a very hard plastic, urea formaldehyde, is formed. However, if the 30 ml is added to the urease-contaminated system instead there is not formed any hard plastic.

It is seen that addition of urease to a urinal system immediately decomposes urea and that the urea formaldehyde plastic cannot be formed with a starting material of liquid manure from a conventional stable system.

Example 3

$Cu^{2+}$-Ion Inhibition of Urease Activity

A way of avoiding the damaging activity of the urease enzyme is to add $Cu^{2+}$-ions to the urinal system. If for example 1 g of copper sulphate, pentahydrate is added to our reference system described in example 1 and then it is contaminated with 1 ml urease, the colour shift of phenolphthalein does not occur, and the contaminated system does not begin to smell of ammonia.

It is seen that the catalytic effect of the urease enzyme on the hydrolysis of urea is completely lost by the presence of $Cu^{2+}$-ions in the urinal system.

Example 4

$Cu^{2+}$-Ion Effect on Formation of Urea Formaldehyde

Now an interesting question is whether the presence of these $Cu^{2+}$-ions described in Example 3 also inhibits the formation of the urea formaldehyde plastic? This can simply be studied by addition of 30 ml of methanal to the urease-contaminated and $Cu^{2+}$-contaminated reference system. The polymerisation proceeds as defined in the reaction equations (2)-(4).

It is seen that it is possible to form the urea formaldehyde plastic in spite of the presence of urease contamination in a urinal system as long as $Cu^{2+}$-ions are present.

Example 5

$Ag^+$- and $Pb^{2+}$-ion Inhibition of Urease Activity

It turns out that not just $Cu^{2+}$ removes the catalytic effect of the urease enzyme on the hydrolysis of urea, $Ag^+$- and $Pb^{2+}$-ions also do—for example when formulated in form of silver nitrate and lead acetate, respectively. For example if 1 g of silver nitrate or 1 g of lead acetate is added to our reference system and it is then contaminated with 1 ml of urease, the colour shift of phenolphthalein does not occur, and the contaminated system does not begin to smell of ammonia.

It is seen then that the catalytic effect on the hydrolysis of urea is completely lost when $Ag^+$- or $Pb^{2+}$-ions are present in the urinal system.

Example 6

$Ag^+$- and $Pb^{2+}$-ion Effects on Formation of Urea Formaldehyde

An interesting question is now whether the presence of these ions also inhibits the formation of the urea formaldehyde plastic? This is simple studied by addition of 30 ml methanal to the reference system contaminated with urease, $Ag^+$- or $Pb^{2+}$-ions. The polymerisation follows as defined in the reaction equations (2)-(4).

It is seen that it is possible to form the urea formaldehyde plastic in spite of an urease-contaminated urinal system—when $Ag^+$- or $Pb^{2+}$-ions are present.

Example 7

Ag$^+$- and Pb$^{2+}$-ion Inhibition of Urease Activity and Formation of Urea Formaldehyde In urease the active centre is constituted among others by Ni$^{2+}$-ions, i.e. if there is no nickel in urease, its catalytic effect is removed. The compound dimethylglyoxime forms, under weak basic conditions, a complex bonding to nickel (II)-ions whereby urease becomes inactive.

Providing a urinal system—consisting of 10 g synthetic urea, diluted with water to 50 ml and adding further 1 ml of ammonia, 1 g dimethylglyoxime and 1 ml urease, a clear red colour can be observed in the glass flask. This colour is caused by the complex formation between dimethylglyoxime and nickel (II); bis(dimethylglyoximato)-nickel (II). If further 30 ml of methanal is added urea polymerises as usual with methanal forming urea formaldehyde.

It is seen that in spite of urease contamination, it is possible to form the urea formaldehyde plastic in an alkaline urinal system when dimethylglyoxime is present.

Example 8

Ethylenediamine Inhibition of Urease Activity and Formation of Urea Formaldehyde and Formation of Urea Formaldehyde Nickel (II)-ions form a strong violet coloured complex compound with ethylenediamine in form of tris(ethylenediamine)-nickel (II).

Providing a urinal system—consisting of 10 g synthetic urea, diluted with water to 50 ml and adding further 1 g ethylenediamine and 1 ml urease, a clear violet colour is seen in the glass flask. If further 30 ml of methanal is added, urea ordinarily polymerises with methanal forming urea formaldehyde.

It is seen that it is possible to form the urea formaldehyde plastic in a urinal system in spite of urease-contamination, when ethylenediamine is present—in a concentration which naturally depends completely on the urease concentration.

Example 9

Formation of Urea Formaldehyde From Urease-free Liquid Manure

The question is now whether the polymerisation reaction can proceed in a common liquid manure system—does there exist one or more chemical components in liquid manure which can inhibit the reaction between urea and methanal? This question is studied by providing a liquid manure system consisting of 10 g synthetic urea, diluted with fresh liquid manure to 50 ml, said manure being taped directly from an upstanding saw and having not been into contact with faeces. Adding further 30 ml, methanal urea polymerises ordinarily with methanal to form urea formaldehyde.

It is seen that there are not unknown chemical components in the liquid manure which inhibits the polymerization process as shown in equations (2)-(4).

Example 10

Formation of Urea Formaldehyde From Concentrated Livestock-Produced Urea—Cu$^{2+}$-ion Inhibition of Urease Activity—Treatment According to the Invention The question is now whether it is possible to concentrate livestock-produced urea from a stable system and then form urea formaldehyde plastic therefrom? This question is studies in the following experiment:

Below a stable floor supporting 20 pigs to be slaughtered a large plastic foil covering the underlying floor having the shape of an inverted pyramid was placed. On this foil 5 l of water and 10 g of copper sulphate, pentahydrate were added. The liquid manure and faeces of the animals were collected on this foil for the next 24 hours. From this foil 20 l sample was collected (and separated) and treated in a hyperfiltration system of the type ROMEDI-250 supplied by UNION-filtration a/s, Nakskov, Denmark. The separation process was continued until a total of 15 l permeate liquid—water was withdrawn. The urea-lean fraction was disposed.

From the retained 5 l concentrate 50 ml was sampled and added 30 ml of methanal—the polymerisation proceeded as previously disclosed above.

It is seen that it is possible
1) to remove the urease activity from natural animal faeces by adding Cu$^{2+}$-ions to the manure system;
2) to concentrate naturally formed urea by a simple pressure-driven separation process;
3) to use naturally formed urea as reactant in a polymerisation reaction with methanal, cf. the equations (2)-(4).

Example 11

Formation of Urea Formaldehyde From Concentrated Livestock-Produced Urea—Other Urease Inhibitors The last of the above disclosed polymerisations experiments can be reproduced when the copper sulphate, pentahydrate is substituted by lead acetate, silver nitrate, dimethylglyoxime or ethylenediamine.

Example 12

Reversible Inhibition by Controlling pH

In a preferred embodiment said reversible inhibition of urease activity comprises treating said collected waste matter by a method comprising decreasing and/or increasing pH. Preferably said pH increase and/or decrease is accomplished by adding a buffer system such as sodium acetate/acetic acetate.

Example 13

Reversible Inhibition by Controlling pH and Urea Retention Time

Controlling the pH of the collected waste matter in the under stable allows selecting a pH close to the isoelectric point of urease, viz. about pH 5.5 for animal waste matter manure. It should be noted that the actual isoelectric point depends on the origin of the urease and the actual conditions. At this pH urease is not completely inhibited but its activity is low and determined by its retention time in the collected waste matter.

In order to arrive at a simple model for retention of urease in the under stable and thereby determined when to empty the under stable to ensure a sufficient low loss, the under stable is considered a simple continuous stirred tank reactor—CSTR—reference is made to FIG. 1 illustrating the situation.

Referring to FIG. 1 a stable system comprises a waste matter collection container for collection of waste matter. In a preferred embodiment said collection container is located in a lower stable 11 below the stable floor of an upper stable 12 for the animals.

The inhibitor 11 inlet to the under stable is here a buffer consisting of sodium acetate and acetate.

The following reaction will occur in the under table

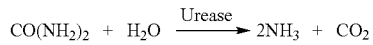

The urea is brought to the under stable, with the volume V, $dm^3$, through the floor separating the over—and under stable. The concentration of the urea inlet is called $C_o$, $mol/dm^3$. The inlet of urea is diluted in a water fraction called urine, with the volume velocity f, $dm^3/min$, which is direct proportional to the number of animals, N, in the over stable, and the average amount of urine, $\bar{f}$, $dm^3/min$, which a single animal will produce per minute. A simple mass balance for the time dependent urea concentration C, $mol/dm^3$, is expressed as $$\tau_m \frac{dC}{dt} + R(C)\tau_m + C = C_o$$

where $$\tau_m \equiv V/f = V/(N\bar{f})$$

is the time constant of the under stable, and where R(C), $mol/min/dm^3$, is the Michaelis-Menten rate expressed as $$R(C) = \frac{v_m}{1 + K_m/C}$$

If we are substituting this expression into the above equation, it follows $$\tau_m \frac{dC}{dt} + \frac{v}{1 + K_m/C}\tau_m + C = C_o$$

At steady state conditions, it clearly follows that $\tau_m dC_s/dt=0$, hence the urea concentration, $C=C_s$, is expressed through $$\frac{v_m}{1 + K_m/C_s}\tau_m + C_s = C_{os} \Rightarrow C_s^2(v_m\tau_m + K_m - C_{os})C_s - K_m C_{os} = 0$$

or $$C_s = \frac{C_{os} - v_m\tau_m - K_m + \sqrt{(v_m\tau_m + K_m - C_{os})^2 + 4C_{os}K_m}}{2}$$

It now follows that the time constant, $\tau_m$, needed to identify $C_s=(1-\eta)C_{os}$; i.e.: 100%·$\zeta$ urea loss, is expressed through $$(1-\eta)C_{os} = \frac{C_{os} - v_m\tau_m - K_m + \sqrt{(v_m\tau_m + K_m - C_{os})^2 + 4C_{os}K_m}}{2}$$

or $$\tau_m = \frac{\eta}{v_m}\left(\frac{1}{1-\eta}K_m + C_{os}\right)$$

Recall the relation: $\tau_m \equiv V/f=V/(N\bar{f})$, through which it is possible to calculate the number of animals per volume of the under stable. If the under stable is old, but must be redesigned for minimizing the loss of urea to ammonia, the volume might measured through a photogrammetrical method (e.g. the "V-star" system from Leica and Nikon).

When pH equals 5.5 in a pig manure system, $v_m$ and $K_m$ equals approximately $2\times10^{-3}$ $mol/dm^3/min$ and $1\times10^{-3}$ $mol/dm^3$, hence $[\tau_m]_{pH=5.5}\approx50$ min when the urea loss is set to 10%. When pH equals 7 in a similar manure system, $v_m$ and $K_m$ equals approximately $11\times10^{-3}$ $mol/dm^3/min$ and $4\times10^{-3}$ $mol/dm^3$, hence $[\tau_m]_{pH=7}\approx9$ min. Both $v_m$ and $K_m$ is determined through a classical Lineweaver-Burk plot described in standard biochemical literature, e.g. see "Biochemistry", Third Edition, Geoffrey Zubay, p. 205-219, WMC-Publishers, ISBN:0-697-14267-1.

Please notice that the urease activity may vary between different manure systems, hence $(v_m, K_m)$ must be treated as a phenomenally set of parameters defined by the actual conditions of a given under stable. Dependent of the composition of the faeces from the animals, some of the urease will diffuse to the urea in the water phase in the under stable. In fact, from a design-engineering point of view, the situation is very similar to transport phenomena known in catalyst pellets.

The pH-value in the under stable is preferably adjusted with a buffer system without using components which pollute the environment and which are compatible the animals. Here a combination of sodium acetate and acetate is used, because it is an nontoxic agent, non-pollutant for the environment, the acid $CH_3COOH$ has the closets pKa-value to 5.5, hence the maximum buffer capacity, hence a minimum amount of the buffer system has to be added to the under stable. The pH-value in this buffer system is expressed as $$pH = pK_a + \log\frac{[Ac^-]}{[NaAc]} \text{ or } \frac{[Ac^-]}{[NaAc]}$$
$$= 10^{pH-pK_a}$$
$$= 10^{5.5-4.76}$$
$$= 5.495.$$

The buffer capacity is calculated through the expression:

$$2.3\left(\frac{[NaAc] + [HAc]}{(K_a + [H^+])^2}\right)K_a[H^+],$$

and one has to design the pH to be constant a time frame comparable to the time constant of the under stable. This means, that it is necessary to make test measurements of pH, and then optionally adjust the buffer capacity. It should be mentioned that the chosen cation in the buffer system could be taken from the list of ionic urease inhibitors according to the invention, see above. One should, however, be aware of an optional use of the urea-lean fraction comprising faeces. If this fraction is to be used as biogas fuel, then the chosen buffer must not adversely affect the involved microorganism of the biogas reactor. For the urea-rich fraction, however, which has been added irreversible urease inhibitor(s) for long time storage at the farm or elsewhere these inhibitors are kept in a close system and therefore environmentally less important.

What is claimed is:

1. A method of treating waste matter from animals, the method comprising:
   a) collecting waste matter from the animals;
   b) inhibiting urease activity in said collected waste matter; and
   c) separating said urease-activity inhibited waste matter into a urea-rich fraction essentially consisting of a liquid comprising urea and other components soluble in liquid manure and a urea-lean fraction;
   d) irreversibly inhibiting urease activity in said urea-rich fraction wherein said irreversible inhibition comprises treating said urea-rich fraction with an irreversible inhibitor, said inhibitor being selected among the group consisting of
   urea compounds selected from the group consisting of hydroxyurea, selenourea, phenylurea and thiourea;
   benzoeates selected from the group consisting of p-substituted mercuribenzoate, p-chloromercuribenzoate, p-hydroxymercuribenzoate and iodosobenzoate;
   p-chloromercuribenzenesulfonate;
   N-ethylmaleimide;
   phosphor compounds selected from the group consisting of phosphoramidate and phosphate;
   monovalent ions selected from the group consisting of $F^-$, $Na^+$, and $K^+$;
   divalent metal ions selected from the group consisting of $Hg^{2+}$, $Cu^{2+}$, $Fe^{2+}$, $Co^{2+}$, $Zn^{2+}$, $Ni^{2+}$, $Mn^{2+}$, $Cd^{2+}$, $Ag^+$, $Mg^{2+}$(weak), $Ba^{2+}$, $Pb^{2+}$,
   and combinations thereof in form of at least one water-soluble salt, and/or at least one electrochemically-released ion;
   $As^{3+}$;
   at least one nickel-complexing agent selected from the group consisting of dimethylglyoxime, ethylenediamine and combinations thereof, and
   compounds selected from the group consisting of beta-mercaptoethanol, iodine, suramin, phenylsulfinate, and furacin;
   e) recovering the urea-rich essentially liquid fraction obtained in step c); and
   f) recovering the urea-lean fraction obtained in step c;
   wherein said inhibition of step b) comprises treating said collected waste matter by a method including at least one step selected from the group consisting of decreasing pH, buffering pH, at least one of decreasing and increasing pressure, at least one of decreasing and increasing ionic strength and combinations thereof.

2. The method according to claim 1, wherein said urea-lean fraction is in form of a liquid, a solid, or a combination thereof, or in form of a dried solid.

3. The method according to claim 1, wherein said irreversible inhibitor is recovered from said irreversibly urease-activity inhibited and separated urea-rich fraction.

4. The method according to claim 1, wherein said waste-matter comprises feces and liquid manure from farm animals.

5. The method according to claim 1, wherein the irreversible inhibitor is at least one divalent metal ion and the divalent metal ions are selected from the group consisting of $Cu^{2+}$, $Ag^+$ and $Pb2+$.

6. A method of producing thermosetting urea-formaldehyde plastic from waste matter of animals, the method comprising:
   a) producing an essentially liquid urea-rich fraction of the waste matter from the animals by a method comprising:
   i) collecting waste matter from the animals;
   ii) inhibiting urease activity in said collected waste matter;
   iii) separating said urease-activity inhibited waste matter into a urea-rich fraction essentially consisting of a liquid comprising urea and other components soluble in liquid manure and a urea-lean fraction; said inhibition comprising reversible inhibiting urease activity of said collected waste matter before said separation of said urease-activity inhibited waste matter into said urea-rich fraction and said urea-lean fraction; and
   iv) irreversibly inhibiting urease activity in said urea-rich fraction, wherein said irreversible inhibition comprises treating said urea-rich fraction with an irreversible inhibitor, said inhibitor being selected among the group consisting of:
   urea compounds selected from the group consisting of hydroxyurea, selenourea, phenylurea and thiourea;
   benzoeates selected from the group consisting of p-substituted mercuribenzoate, p-chloromercuribenzoate, p-hydroxymercuribenzoate and iodosobenzoate;
   p-chloromercuribenzenesulfonate;
   N-ethylmaleimide;
   phosphor compounds selected from the group consisting of phosphoramidate and phosphate;
   monovalent ions selected from the group consisting of $F^-$, $Na^+$, and $K^+$;
   divalent metal ions selected from the group consisting of $Hg^{2+}$, $Cu^{2+}$, $Fe^{2+}$, $Co^{2+}$, $Zn^{2+}$, $Ni^{2+}$, $Mn^{2+}$, $Cd^{2+}$, $Ag^+$, $Mg^{2+}$(weak), $Ba^{2+}$, $Pb^{+2}$ and combinations thereof in form of at least one water-soluble salt, and/or at least one electrochemically-released ion;
   $As^{3+}$;
   at least one nickel-complexing agent selected from the group consisting of dimethylglyoxime, ethylenediamine and combinations thereof, and
   compounds selected from the group consisting of beta-mercaptoethanol, iodine, suramin, phenylsulfinate, and furacin, and
   b) reacting said urea-rich fraction with methanal.

7. The method according to claim 6, wherein said waste matter comprises feces and liquid manure from farm animals.

8. The method according to claim 6, wherein said irreversible inhibitor comprises divalent metal ions selected from the group consisting of $Cu^{2+}$, $Ag^{30}$ and $Pb^{2+}$ and combinations thereof.

9. The method according to claim 6, wherein said separating step comprises centrifugation or filtration.

10. The method according to claim 9, said method further comprising subjecting said urea-rich fraction to ultra-filtration to produce a urea-rich permeate.

11. The method according to claim 10, said method further comprising subjecting said urea-rich permeate to nano-filtration to produce a urea-rich nano-filtered permeate.

12. The method according to claim 11, said method further comprising subjecting said urea-rich nano-filtered permeate to hyper-filtration to produce a urea-rich concentrate.

13. The method according to claim 6, wherein the urea-rich fraction is reacted with methanal under acidic conditions.

14. The method according to claim 6 further comprising concentrating the urea formaldehyde product.

* * * * *